(12) United States Patent
Holte

(10) Patent No.: US 7,572,235 B2
(45) Date of Patent: Aug. 11, 2009

(54) METHOD AND SYSTEM OF MEASURING IAP USING A NASO-ENTERIC TUBE

(75) Inventor: Bo Holte, Charlottenlund (DK)

(73) Assignee: Holtech Medical, Charlottenlund (DK)

( * ) Notice: Subject to any disclaimer, the term of this patent is extended or adjusted under 35 U.S.C. 154(b) by 0 days.

(21) Appl. No.: 11/683,693

(22) Filed: Mar. 8, 2007

(65) Prior Publication Data

US 2007/0282307 A1 Dec. 6, 2007

Related U.S. Application Data

(63) Continuation-in-part of application No. 11/445,715, filed on Jun. 2, 2006.

(51) Int. Cl.
*A61B 5/00* (2006.01)
(52) U.S. Cl. ..................................... 600/561
(58) Field of Classification Search ............... 600/561, 600/403, 587, 300; 604/27, 30, 65
See application file for complete search history.

(56) References Cited

U.S. PATENT DOCUMENTS

| | | | |
|---|---|---|---|
| 3,860,000 A * | 1/1975 | Wootten et al. | 604/28 |
| 3,980,082 A | 9/1976 | Miller | |
| 4,170,224 A | 10/1979 | Garrett et al. | |
| 4,184,484 A | 1/1980 | Wright et al. | |
| 4,217,911 A | 8/1980 | Layton | |
| 4,696,672 A | 9/1987 | Mochiuzki et al. | |
| 4,711,248 A | 12/1987 | Steuer et al. | |
| 4,727,887 A | 3/1988 | Haber | |
| 4,790,328 A | 12/1988 | Young | |
| 4,841,984 A | 6/1989 | Armeniades et al. | |
| 5,211,642 A | 5/1993 | Clendenning | |
| 5,433,216 A * | 7/1995 | Sugrue et al. | 600/591 |
| 6,503,208 B1 | 1/2003 | Skovlund | |
| 2004/0054350 A1 * | 3/2004 | Shaughnessy et al. | 604/535 |
| 2006/0079804 A1 | 4/2006 | Sugrue et al. | |

FOREIGN PATENT DOCUMENTS

WO 86/00534 A1 1/1986

(Continued)

OTHER PUBLICATIONS

"Revision of the original Kron method for intravascular pressure measurement" by Cheatham and Safcsak, Intensive Care Medicine, Dec. 1999 p. 1454.*

(Continued)

*Primary Examiner*—Kevin C Sirmons
*Assistant Examiner*—Deanna K Hall
(74) *Attorney, Agent, or Firm*—Andrus, Sceales, Starke & Sawall, LLP

(57) ABSTRACT

A method and apparatus for measuring the intra-abdominal pressure (IAP) within a patient having a naso-enteric tube. The system senses the IAP of the patient by means of a fluid filled sensing conduit that transmits the pressure in the naso-enteric tube to a pressure measuring device such as a pressure transducer or a manometer tube. The sensing fluid in the sensing conduit may be saline, air, or feeding solution. When a pressure transducer is used, the IAP is determined and displayed on a patient monitor. Alternatively, the IAP may be determined from the height of the sensing fluid within the sensing conduit.

17 Claims, 7 Drawing Sheets

FOREIGN PATENT DOCUMENTS

WO    2004/078235 A2    9/2004

OTHER PUBLICATIONS

"Bedside measurement of intra-abdominal pressure (IAP) via an indwelling naso-gastric tube: clinical validation of the technique", Collee et al., Intensive Care Medicine, 1993, pp. 478-780.

Revision of the original Kron method for intravascular pressure measurement by CHEATHAM and SAFCSAK, Intensive Care Medicine, Dec. 1999 p. 1454.

"The Measurement of Intra-abdominal Pressure as Criterion for Abdominal Re-exploration", Kron et al., Department of Surgery, University of Virginia Medical Center, vol. 199, No. 1, Jun. 15, 1983, pp. 28-30.

International Search Report and Written Opinion, Dec. 19, 2007.

* cited by examiner

METHOD AND SYSTEM OF MEASURING IAP USING A NASO-ENTERIC TUBE

CROSS-REFERENCE TO RELATED APPLICATION

The present application is a continuation-in-part application that claims priority to U.S. patent application Ser. No. 11/445,715, filed Jun. 2, 2006.

BACKGROUND OF THE INVENTION

The present invention generally relates to a system and method that is useful in the measurement of the pressure within the human body abdominal cavity. More specifically, the present invention relates to a method and system useful with a patient being fed through a naso-enteric feeding tube to determine the intra-abdominal pressure of the patient.

The measurement of intra-abdominal (or intra-visceral) pressure is routinely made in the clinical management of critically ill patients, or patients undergoing major surgery. Typically, the urinary bladder is the preferred site for the pressure measurement, but other hollow organs, such as the stomach or small intestines, may be used as well.

As an example, the Skovlund U.S. Pat. No. 6,503,208 discloses a method and apparatus that returns a volume of collected urine from the patient back to the patient's bladder to determine the intra-abdominal pressure for the patient. The system includes a tube having a series of markings that allows a clinician to obtain a manual measurement of the intra-abdominal pressure of the patient. Although the method and system of the '208 patent provides an accurate measurement of the intra-abdominal pressure for the patient, the system requires a manual measurement to be taken by an attending clinician. Further, once the measurement has been taken, the measurement must be manually entered into an electronic database or monitoring system. Thus, a need exists for a system for monitoring the intra-abdominal pressure of a patient and displaying the sensed pressure on an automated basis.

Many critically ill patients in the intensive care unit (ICU) receive enteral feeding from a naso-enteric feeding tube placed through the patient's nose and into the stomach or small intestine. Outside of the patient, the feeding tube is connected to a container of liquid feed solution by means of a disposable feeding set. The feeding set typically extends between the feeding tube and the liquid feed container through a roller pump that is operable to manage the rate of supply of the feeding solution to the patient.

Early enteral feeding of intensive care patients is accepted as the best way to make sure that the intensive care patient is not starving, as well as for normalizing the patient's digestive functions. Since a high proportion of these patients have intra-abdominal hypertension (IAH), it is desirable to monitor these patients' IAP continuously, on a patient monitor.

SUMMARY OF THE INVENTION

The present invention relates to a method and system for determining the intra-abdominal pressure (IAP) of a patient. Specifically, the present invention relates to a system and method that monitors the pressure in the feeding set or feeding tube to determine the intra-abdominal pressure within the patient.

In one embodiment of the present invention, the patient includes a naso-enteric feeding tube that extends through the patient's nose and into the stomach or as far as the small intestines. One end of the feeding tube extends outside of the patient and is typically configured to receive the supply of liquid feed solution from the feeding pump. The system of the first embodiment provides a specially designed feeding set that includes a supply conduit having a first end connected to the feeding tube of the patient and a second end that extends through the feeding pump to the supply of liquid feed solution. The liquid feed solution is pumped by the feeding pump through the supply conduit to the patient through the feeding tube.

The supply conduit of the first embodiment of the invention includes a sensing conduit that is joined to the supply conduit between its first end and the feeding pump. The first end of the sensing conduit is integrally formed with the supply conduit and extends as a branch away from the supply conduit. The second end of the sensing conduit is configured to receive a pressure transducer. Prior to connecting the pressure transducer to the second end of the sensing conduit, the pressure transducer is vented to atmospheric pressure while the electronic pressure monitoring circuit is calibrated to 0 mmHg in a conventional manner.

After the pressure transducer has been connected to the second end of the sensing conduit, the operation of the feeding pump is started. When the supply conduit and the naso-enteric feeding tube have been filled with the feed solution, a volume of feed solution enters the sensing conduit and compresses the volume of air trapped between the pressure transducer and the volume of feed solution. When the junction point between the feed solution and the entrapped air within the sensing conduit is placed at the patient's mid-axillary line, the total air pressure Pt in the sensing conduit equals the intra-gastric pressure plus a pressure difference of $dP = F \times R$ where F is the flow rate of the feed solution and R is the flow resistance.

The pressure transducer senses the pressure of air within the sensing conduit and generates a signal based upon the sensed pressure. At low flow rates dP will be small compared to the intra-gastric pressure and the pressure measurement from the pressure transducer will closely reflect IAP. At high flow rates, or if the supply conduit or the feeding tube is obstructed, dP may give rise to a substantial overestimation of the IAP. For this reason, the feeding pump should be stopped from time to time in order to determine both the correct IAP value and to detect any obstruction of the supply conduit or feeding tube. In the first embodiment of the invention, the pressure transducer is connected to a patient monitor such that the patient monitor can display the pressure signal received from the pressure transducer.

In an alternate embodiment of the invention, a pressure adapter is positioned between the patient's feeding tube and the supply conduit of the feeding set such that the supply of liquid feed solution passes through the pressure adapter before being received by the feeding tube. Specifically, the pressure adapter includes a first end that receives the liquid feed solution from the feeding pump and a second end that is configured to be received by the feeding tube. The pressure adapter further includes a sensing conduit that is in fluid communication with the pressure adapter at a point between the first and second ends of the pressure adapter. The second end of the sensing conduit receives the pressure transducer such that a volume of air is entrapped within the sensing conduit between the first and second ends of the sensing conduit. Like the first embodiment discussed above, the interface between the feed solution and the air volume in the sensing conduit is positioned at the mid-axillary line of the patient and the operation of the feeding pump is interrupted from time to time to determine the correct IAP and to reveal any obstructions in the supply conduit or the feeding tube. The pressure of the air within the sensing conduit is related to the patient's intra-abdominal pressure and is sensed by the pressure transducer. Preferably, the pressure transducer is connected to a patient monitor such that the patient monitor can display the pressure signal continuously.

In yet another alternate embodiment of the invention, the normal feeding tube used with a patient can be replaced by a naso-enteric feeding tube that includes two, separate lumens. The first lumen of the dual lumen naso-enteric feeding tube receives the supply of liquid feed solution from the feeding pump. The second lumen of the feeding tube extends from the patient's stomach to a second end positioned outside of the patient. The second end of the second lumen receives an air-filled sensing conduit having a second end connected to a pressure transducer. Since the position of the liquid-to-air junction in the sensing conduit varies with pressure, the air pressure within the sensing conduit is directly related to the intra-abdominal pressure of the patient. The pressure transducer is connected to a patient monitor such that the patient monitor can continuously display the intra-abdominal pressure for the patient.

In still another embodiment of the invention, the sensing conduit joined to the supply conduit includes a pressure transducer connected to the second end of the sensing conduit. Once the pressure transducer has been connected to the second end of the sensing conduit, the sensing conduit is filled with physiological saline and the feeding pump is started. When the supply conduit and the naso-enteric feeding tube have been filled with the feed solution, the pressure transducer is placed at a suitable reference level, such as even with the patient's mid-axillary line. When the pressure transducer is positioned even with the mid-axillary line, the total pressure Pt sensed in the sensing conduit by the pressure transducer equals the intra-gastric pressure plus a pressure difference of $dP=F \times R$, where F is the flow rate of the feed solution and R is the flow resistance. The pressurized bag of sterile physiological saline may be connected to the pressure transducer for a continuous low flow (typically 3 ml/hour) or intermittent flushing of the pressure transducer, the sensing conduit, the supply conduit and the naso-enteral feeding tube.

In this embodiment, the pressure transducer senses the fluid pressure within the sensing conduit and generates a signal based upon the sensed pressure. At low flow rates dP will be small compared to the intra-gastric pressure and the pressure measurement from the pressure transducer will closely reflect IAP. At high flow rates, or if the supply conduit or feeding tube is obstructed, dP may give rise to a substantial overestimation of the IAP. For this reason, the feeding pump should be stopped from time to time in order to determine both the correct IAP value and to detect any obstruction of the supply conduit or feeding tube. Like previous embodiments, the pressure transducer is connected to a patient monitor such that the patient monitor can display the pressure signal received from the pressure transducer.

In yet another alternate embodiment, a pressure adapter is positioned between the patient's feeding tube and the supply conduit of the feeding set such that the supply of liquid feed solution passes through the pressure adapter before being received by the feeding tube. The pressure adapter includes a first end that receives the liquid feed solution from the feeding pump and a second end that is configured to be received by the feeding tube. The pressure adapter further includes a sensing conduit that is in fluid communication with the pressure adapter at a point between the first and second ends of the pressure adapter. The second end of the sensing conduit is connected to the pressure transducer. The sensing circuit is filled with a sterile saline and placed at a suitable reference level, such as the mid-axillary line of the patient. The pressure transducer is connected to the patient monitor that displays the correct intra-gastric pressure whenever the feeding pump is stopped temporarily. In addition to sensing the intra-abdominal pressure, the sterile saline can be used to flush the pressure transducer, the sensing conduit and the enteral feeding tube. This embodiment may be used to monitor IAP when disconnected from the supply conduit and feeding pump. In this case, the first end of the pressure adapter is plugged and the supply of saline is directed to the patient.

In yet another alternate embodiment, the sensing conduit is a vertical transparent manometer tube in fluid communication with the supply conduit and includes an air filter that allows equilibration to atmospheric pressure. During pressure measurement, the manometer tube is partially filled with feed solution. The air filter thus prevents bacteria from entering the manometer tube. The height of the fluid column in the manometer tube reflects the intra-gastric pressure provided that a suitable reference point is chosen on the tube, such as the level of the stomach. The height of the fluid column may be measured with a ruler or similar device that is calibrated in mmHg, or a scale that may be printed directed on the manometer tube. The height of the fluid column Pt equals the intra-gastric pressure plus a pressure difference $dP=F \times R$ where F is the flow rate of the feed solution and R is the flow resistance. As described in the previous embodiments, the feeding pump should be stopped from time to time to determine both the correct intra-gastric pressure (IAP) and to detect any obstruction of the supply conduit or enteral feeding tube.

Various other features, objects and advantages of the invention will be made apparent from the following description taken together with the drawings.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
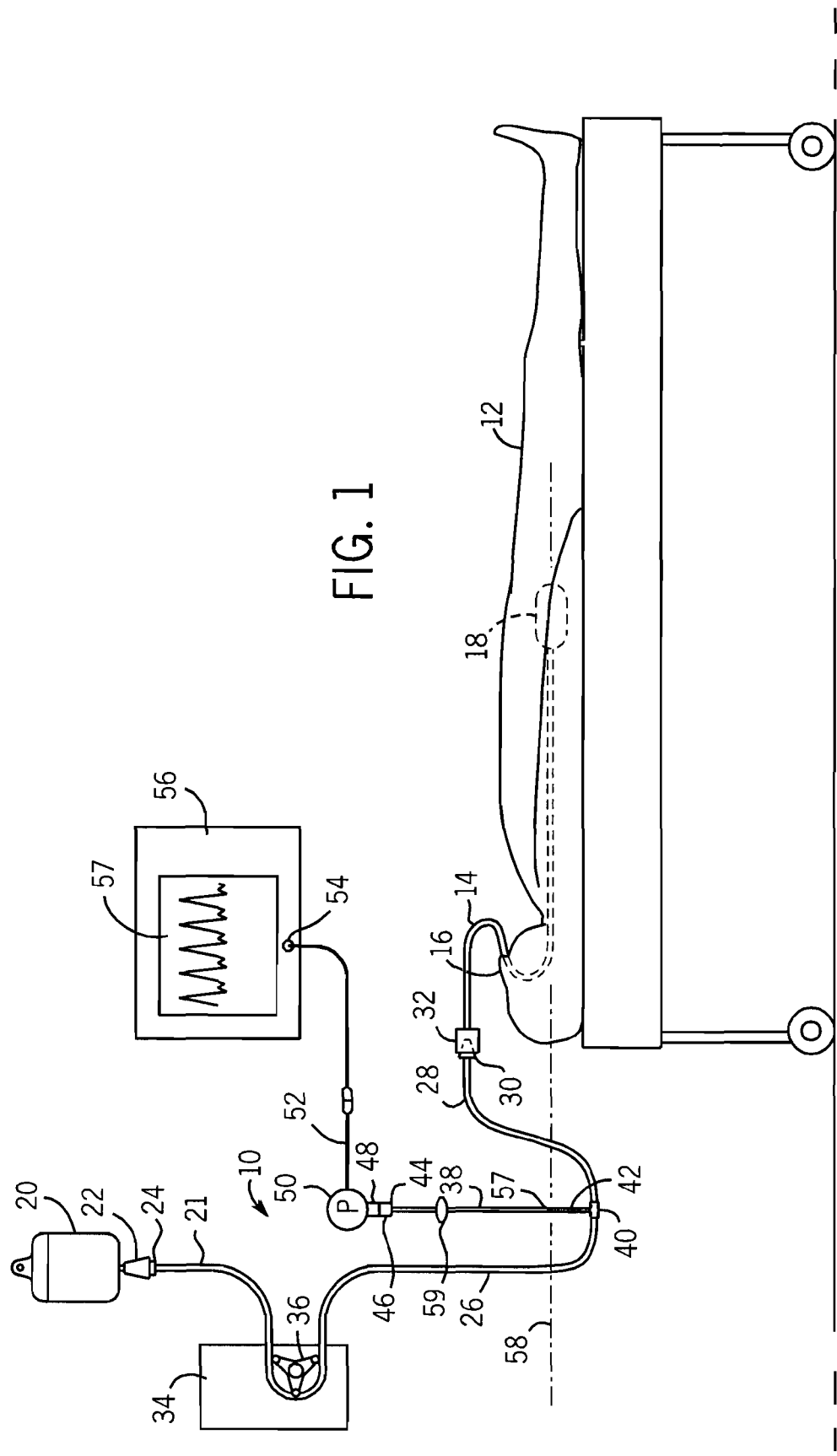
FIG. 1 is an illustration of the intra-abdominal pressure measuring device of the present invention as attached to a patient monitoring device having a display.

FIG. 1 illustrates the intra-abdominal pressure measuring apparatus 10 of the present invention as being utilized with a patient 12 in a post-operative or intensive care environment.

As illustrated in FIG. 1, the patient 12 is in a supine position with a naso-enteric feeding tube 14 extending through the patient's nose 16 and being received within the stomach 18 or the jejunum. The naso-enteric feeding tube 14 allows a supply of liquid feed solution to be fed into the patient's stomach 18 from a supply bag 20.

In the embodiment of the invention illustrated in FIG. 1, the supply bag 20 includes a female connector 22 that receives a male connector 24 formed as part of a supply conduit 26. The second end 28 of the supply conduit 26 also includes a male connector 30 that is received by a female connector 32 formed as part of the feeding tube 14.

The supply of liquid feed solution from the supply bag 20 is pumped into the patient's stomach 18 by an enteral feeding pump 34, such as the Kangaroo Pump available from the Kendall Medical Company. The feeding pump 34 includes a roller assembly 36 that rotates to push the liquid feed solution through the supply conduit 26 and into the stomach 18 of the patient 12. As can be understood in FIG. 1, the supply conduit 26 is fed through the feeding pump 34 and is connected at its first end 21 to the supply bag 20 and at its second end 28 to the feeding tube 14.

In the first embodiment of the invention shown in FIG. 1, a sensing conduit 38 is connected to the supply conduit 26 at a connection point 40. Specifically, a first end 42 of the hollow, tubular sensing conduit 38 is connected to and in fluid communication with the supply conduit 26 at a point between the feeding pump 34 and the second end 28 of the supply conduit 26. In the embodiment of the invention illustrated, the supply conduit 26 includes a T-shaped connector positioned within the supply conduit 26 and having a branch connected to the first end 42 of the sensing conduit 38. The sensing conduit 38 is a hollow tube that extends from the first end 42 to a second end 44.

The second end 44 of the sensing conduit 38 includes a coupling 46 that receives a mating coupling 48 of a pressure transducer 50. The pressure transducer is a conventional component, such as the TrueWave disposable pressure transducer available from Edwards Lifesciences, and generates a signal along the output line 52 that relates to the air pressure sensed by the pressure transducer 50. The output line 52 can be received by an input 54 of a patient monitor 56 such that the patient monitor can display the pressure measurements from the transducer 50 on a display 57 on a continuous or intermittent basis.

As can be understood in FIG. 1, when the pressure transducer 50 is attached to the second end 44 of the sensing conduit 38, a volume of air is entrapped within the sensing conduit 38. The trapped volume of air within the sensing conduit 38 allows the pressure transducer to make a pressure determination of the fluid in the supply conduit 26, as determined at the air-to-liquid junction 57.

Referring back to FIG. 1, when the liquid feed solution is being supplied to the patient from the supply bag 20, the liquid feed solution is directed to the patient through the supply conduit 26 at a programmable flow rate. As the liquid feed solution is being pumped through the supply conduit 26, a volume of the feed solution enters into the sensing conduit 38. As the liquid feed solution enters into the sensing conduit 38, the liquid feed solution meets the volume of air at a liquid-to-air junction point 57. When the volume of feed solution enters the sensing conduit 38, the feed solution compresses the air trapped between the pressure transducer and the point 57, which is the air-to-fluid junction within the sensing conduit 38. When the junction point 57 is placed at the level of the patient's mid-axillary line 58, the total air pressure Pt in the sensing conduit 38 equals the intra-gastric pressure plus a pressure difference $dP=F \times R$, where F is the flow rate of the feeding solution and R is the flow resistance. The pressure transducer senses the pressure of air within the sensing conduit and generates a signal based upon the sensed pressure. At low flow rates, dP will be small compared to the intra-gastric pressure and the pressure will closely reflect IAP. At high flow rates, or if the supply conduit or the feeding tube are obstructed, dP may give rise to a substantial overestimation of IAP. For this reason, the operation of the feeding pump should be stopped from time to time in order to determine the correct IAP value and to detect any obstruction of the supply conduit or feeding tube.

If the junction point 57 is positioned at the mid-axillary line 58 of the patient, the pressure of the volume of air within the sensing conduit will equal Pt for the patient 12. The IAP for a patient has been demonstrated to be identical to the intra-gastric pressure when the patient's mid-axillary line is used as the zero pressure reference level. The greater the IAP for the patient, the higher the feed solution will travel up into the sensing conduit 38. The compression of the air within the sensing conduit 38 will thus be sensed by the pressure transducer 50, which provides a signal to the patient monitor 56 that is related to the IAP for the patient 12. Thus, the IAP for the patient 12 can be determined by positioning the junction point 57, which is the junction between the liquid feed solution and the air volume in the sensing conduit 38 at the level of the patient's mid-axillary line. Once the pressure transducer 50 determines the pressure within the sensing conduit 38, the sensed value is relayed to the patient monitor 56.

Prior to recording the intra-abdominal pressure for the patient using the pressure transducer 50, the operation of the feeding pump 34 is suspended. When the feeding pump is supplying the liquid feed solution to the patient, a pressure gradient can be developed between the junction point 57 at the mid-axillary line and the tip of the feeding tube inside of the patient. Although this "error" will be very small at the normal flow rate of liquid feed solution, a more accurate measurement can be obtained when the operation of the feeding pump is interrupted. As an example, a very high pressure value could be detected by the pressure transducer 50 when the supply conduit is partially clogged between the junction point 57 and the tip of the feeding tube, since the feeding pump 34 can create very high pumping pressure. Thus, in the most preferred embodiment of the invention, the operation of the feeding pump 34 is interrupted during the recording of an IAP measurement from the patient.

In the preferred embodiment of the invention shown in FIG. 1, the supply conduit 26 and the sensing conduit 38 are integrally formed as part of a single, disposable feeding set. The disposable feeding set includes a sterile in-line filter 59 that is placed in the sensing conduit 38 to prevent contamination of the liquid feed solution being supplied to the patient. The in-line filter 59 enables the use of the same pressure transducer with multiple different disposable feeding sets. The feeding set includes separate connections to the feeding tube 14, the supply bag 20 and the pressure transducer 50. Once the feeding set has been used with a patient for a certain period of time, the feeding set can be disposed of and a new feeding set used with the same pressure transducer. Although a specific type of feeding pump 34 and pressure transducer 50 have been shown and described in the preferred embodiment of the invention, various other feeding pumps and pressure transducers can be utilized while operating within the scope of the present invention.

Figure 2:
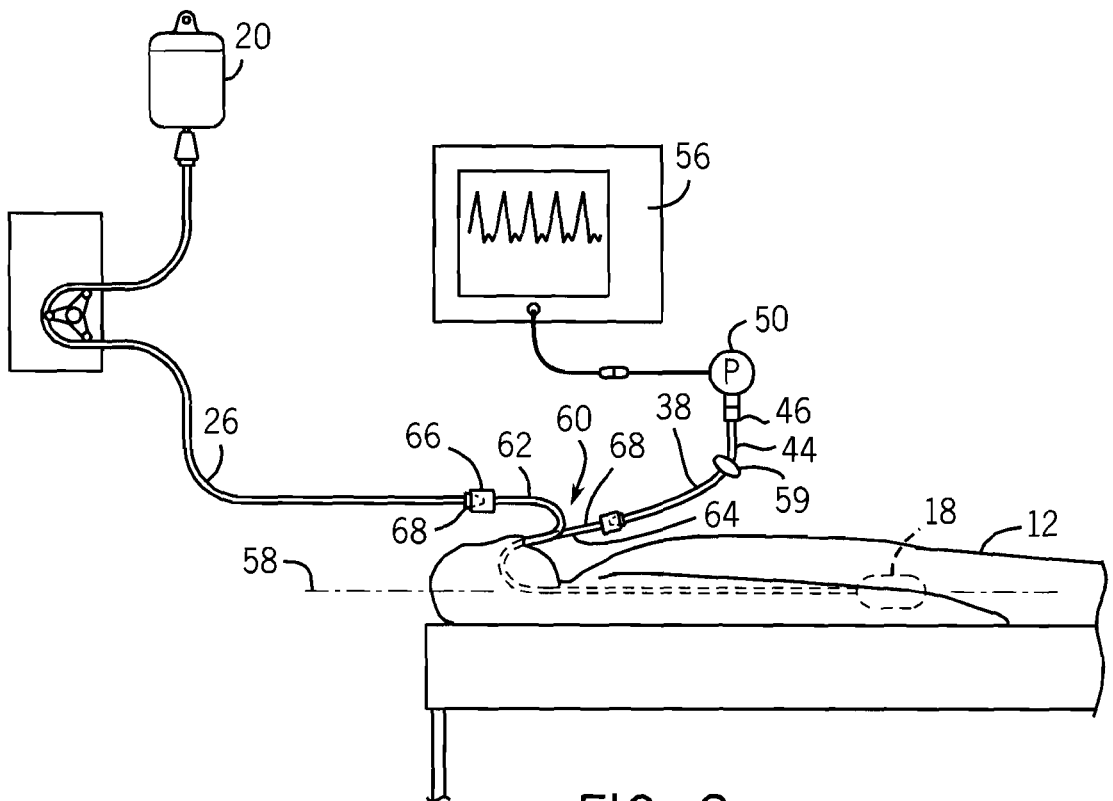
FIG. 2 is an illustration of a first alternate configuration of the intra-abdominal pressure measuring device.

Referring now to FIG. 2, thereshown is a second embodiment of the present invention, where like reference numerals are used for similar components. In the embodiment illustrated in FIG. 2, a specialized feeding tube 60 is utilized. Specifically, the feeding tube 60 is a dual-lumen feeding tube that includes a first lumen 62 and a second lumen 64. As shown, the first lumen 62 includes a female connector 66 that receives a mating male connector 68 of the supply conduit 26. The first lumen 62 extends into the patient's stomach 18 and supplies the liquid feed solution to the patient 12.

The second lumen 64 of the dual-lumen feeding tube 60 includes a first end that extends into the patient's stomach and a second end 68 that extends out of the patient and receives the sensing conduit 38. In a preferred embodiment of the invention, the second lumen 64 is in fluid communication with the patient's stomach and the sensing conduit 38 is filled with air once the pressure transducer 50 is coupled to the connector 46 on the second end 44 of the sensing conduit 38. Since the first end of the second lumen 64 extends into the patient's stomach 18, the end of the second lumen 64 is at the mid-axillary line 58 of the patient.

When the pressure transducer 50 is connected to the second lumen 64, a small volume of fluid fills the second lumen 64 and compresses the air volume contained within the sensing conduit 38. The air pressure within the sensing conduit 38 is sensed by the pressure transducer 50, which relays signals to the patient monitor 56 for display.

As can be understood in FIG. 2, the dual-lumen feeding tube 60 allows for the direct monitoring of the IAP for the patient 12 by utilizing the second lumen 64, which is separate from the first lumen 62 used to supply the liquid feed solution to the patient 12. Although this system functions very well to determine the IAP for the patient 12, it requires a specialized feeding tube 60 which may not be currently available in most critical care environments.

Figure 3:
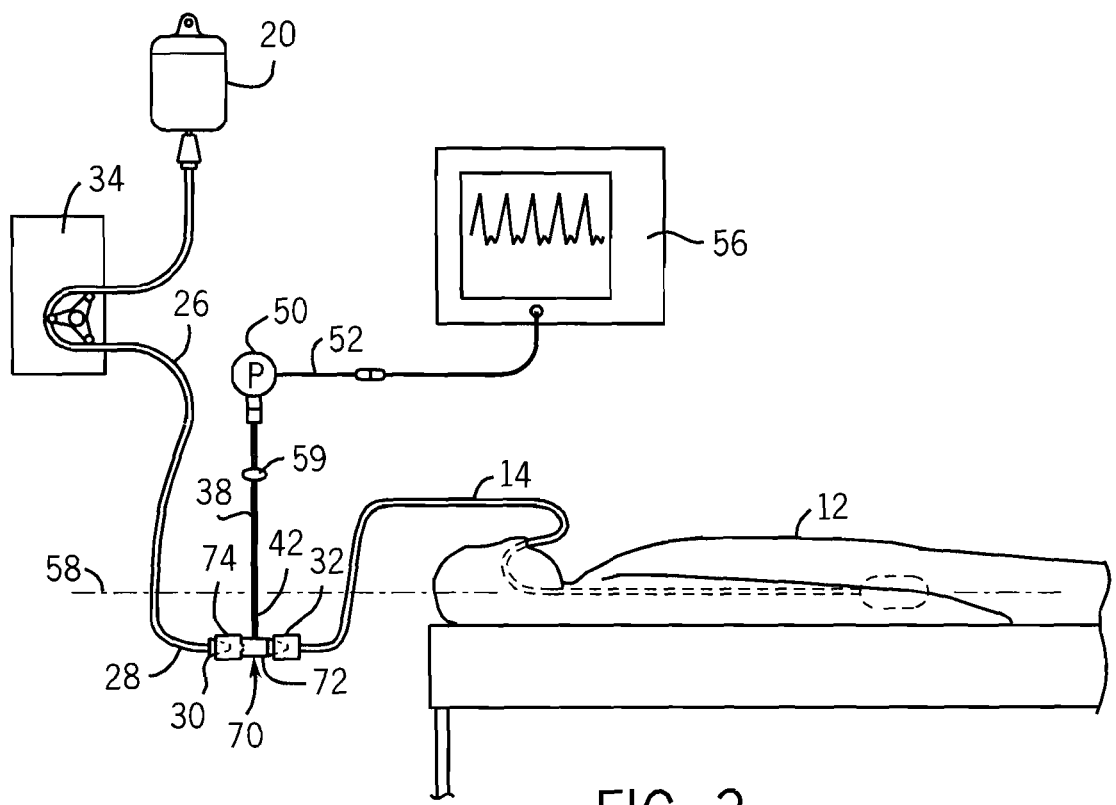
FIG. 3 is a second, alternate configuration of the intra-abdominal pressure measuring device in accordance with the present invention.

Referring now to FIG. 3, thereshown is yet another alternate embodiment of the present invention. In the embodiment shown in FIG. 3, the female connector 32 of the feeding tube 14 receives a pressure adapter 70. The pressure adapter 70 includes a main body 72 having a male connector received within the female connector 32 and a female connector 74 that receives the male connector 30 formed as part of the supply conduit 26. Thus, the supply of liquid feed solution from the supply bag 20 is pumped by the feeding pump 34 through the body 72 of the pressure adapter 70 and into the feeding tube 14.

As shown in FIG. 3, the first end 42 of the sensing conduit 38 enters into the main body 72 between the female connector 74 and the male connector 72. Preferably, the sensing conduit 38 is integrally formed with the patient adapter 70 such that the entire combination of the patient adapter 70 and the sensing conduit 38 can be supplied as a single, disposable unit.

As described in the first embodiment shown in FIG. 1, the pressure within the patient 12 causes a volume of the liquid feed solution to enter into the sensing conduit and compress the volume of air within the sensing conduit 38. To obtain a pressure measurement, the junction point 57 between the liquid feed solution and the volume of air is positioned at the mid-axillary line 58. After the operation of the feeding pump 34 has been suspended, the pressure signal from the pressure transducer 50 is directly related to the pressure within the patient 12 and can be recorded by the patient monitor 56. Preferably, the sensing conduit 38 includes the air filter 59 to prevent contamination of the feed solution being supplied to the patient.

The embodiment shown in FIG. 3 can be utilized with a standard feeding tube 14 and supply conduit 26 by simply inserting the pressure adapter 70 at the normal connection point between the feeding tube 14 and the supply conduit 26. As indicated, the sensing conduit 38 is preferably integrally formed with the main body 72 and air filter 59 and can be applied as a single unit that can then be connected to the pressure transducer 50.

Figure 4:
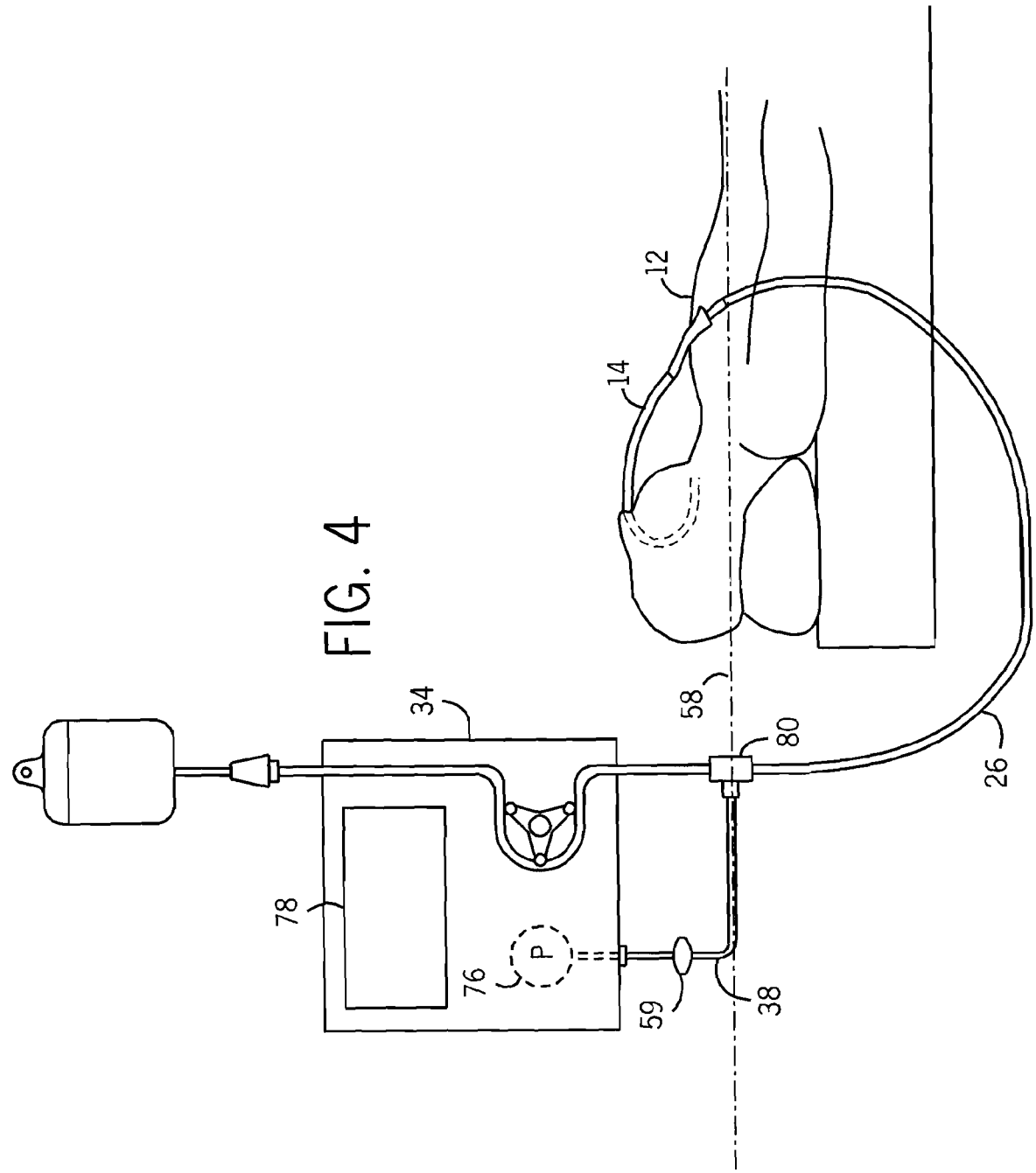
FIG. 4 is a third, alternate configuration of the intra-abdominal pressure measuring device in accordance with the present invention.

Referring now to FIG. 4, thereshown is yet another embodiment of the present invention. In the embodiment shown in FIG. 4, the feeding pump 34 includes an internal pressure transducer 76 that operates in the same manner as the pressure transducer 50 shown in FIGS. 1-3. In the embodiment shown in FIG. 4, the sensing conduit 38 is in fluid communication with the supply conduit 26 and includes the air filter 59 with a connector 80 that connects with a mating connector mounted on the feeding pump 34. As in the previous embodiments discussed, the air-to-liquid junction within the sensing conduit 38 is placed at the mid-axillary line 58 of the patient 12 such that the pressure transducer 76 can determine the IAP for the patient 12. In the embodiment shown in FIG. 4, the feeding pump 34 includes a display 78 that is operable to display the sensed IAP for the patient.

In the embodiment shown in FIG. 4, the feeding pump 34 is programmed to interrupt operation at a pre-set time interval in order to measure the true pressure in the patient's stomach or jejunum. During the pump's standstill, the pressure signal can be processed electronically to filter out any unwanted signals and extract the desired signals, such as the minimum pressure level during a respiration cycle, and the pressure variations related to the heart pumping activity. The display 78 on the feeding pump 34 can display the derived measurements as described.

When the feeding pump 34 begins to operate, the processor within the feeding pump 34 can calculate the pressure, which now includes the pressure originating from the flow multiplied by the flow resistance between the T-adapter 80 and the end of the feeding tube 14. The feeding pump 34 can continuously monitor for any major or minor occlusion in the supply line 26 or feeding tube 14 and may generate a warning to replace the feeding set or feeding tube.

As can be understood by the above description, the method and apparatus of the present invention utilizes the pressure in the feeding set or feeding tube as an indication of the IAP for the patient 12. The pressure transducer senses the air pressure within a sensing conduit which is directly related to the IAP for the patient 12. The pressure transducer provides a pressure signal to the patient monitor 56 or display 76, which can then display the IAP for the patient on a continuous or intermittent basis.

Figure 5:
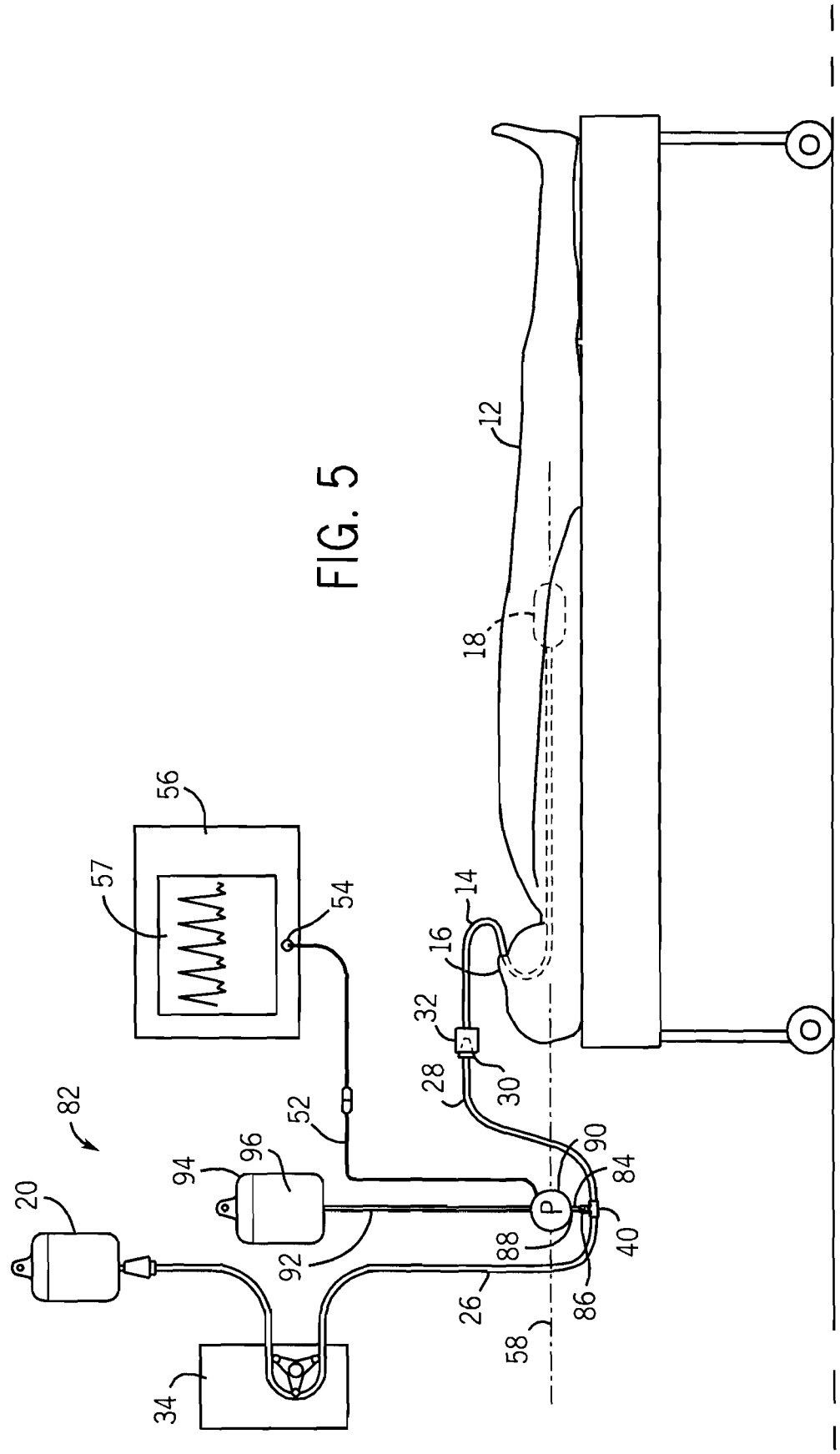
FIG. 5 is a fourth, alternate configuration of the intra-abdominal pressure measuring device that utilizes a supply of sterile saline to determine the intra-abdominal pressure.
Figure 6:
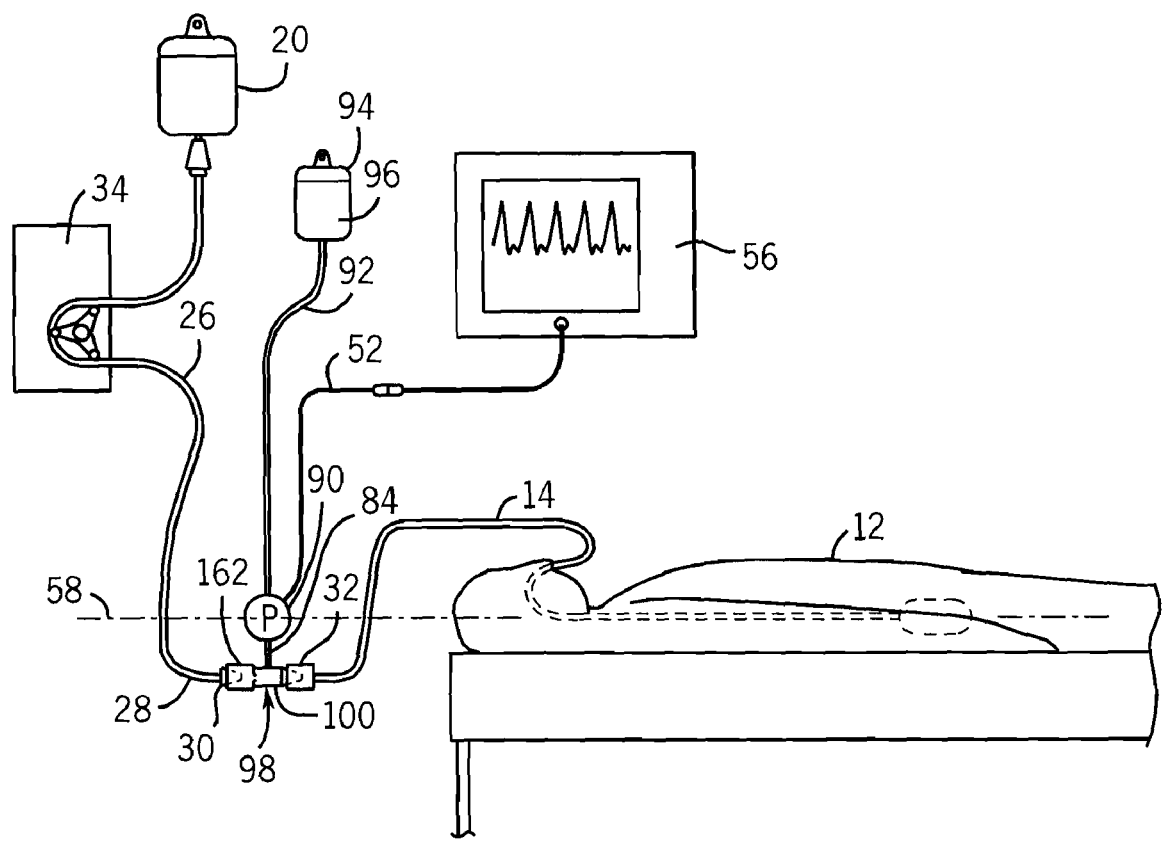
FIG. 6 is a fifth, alternate configuration of the intra-abdominal pressure measuring device.
Figure 7:
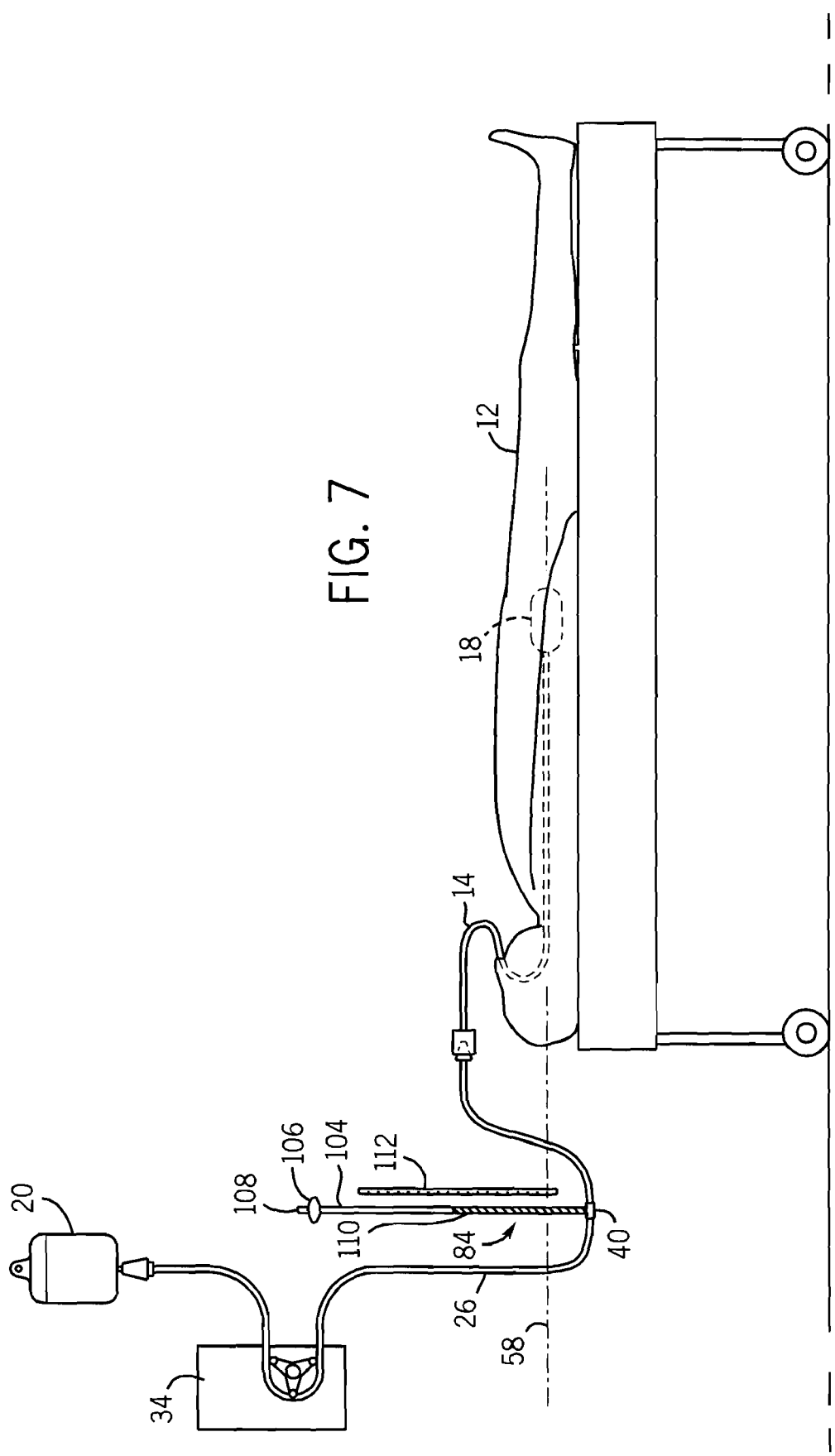
FIG. 7 is a sixth, alternate configuration of the intra-abdominal pressure measuring device in accordance with the present invention.

FIGS. 5-7 illustrate additional embodiments of the invention, where similar reference numerals are utilized to refer to similar components to those shown in the embodiments of FIGS. 1-4. Similar reference numerals are utilized to facilitate understanding.

In the embodiment shown in FIG. 5, the IAP measuring system and apparatus 82 includes the feeding pump 34 that pumps a supply of a liquid feed solution to the patient's stomach 18 from the supply bag 20. Specifically, the supply of liquid feed solution flows through the supply conduit 26 and into the naso-enteric feeding tube 14 through a male connector 30 and a female connector 32. The IAP apparatus 82 includes a sensing conduit 84 that is connected to the supply conduit 26 at the connection point 40. Specifically, a first end 86 of the hollow, tubular sensing conduit 84 is connected to and is in fluid communication with the supply conduit 26 at a point between the feeding pump 34 and the second end 28 of the supply conduit. In the embodiment of the invention illustrated, the supply conduit 26 includes a T-shaped connector positioned within the supply conduit 26 and having a branch connected to the first end 86 of the sensing conduit 84.

A second end 88 of the sensing conduit 84 receives a pressure transducer 90, which is a conventional component similar to the pressure transducer 50 described in the previous embodiments. The pressure transducer 90 generates a signal along the output line 52 that relates to the pressure sensed by the transducer 90. The output line 52 is received by an input 54 of the patient monitor 56 such that the patient monitor 56 can display the pressure measurements from the transducer 90.

As illustrated in FIG. 5, the pressure transducer 90 receives a fluid conduit 92 extending from a supply bag 94 that includes a sensing fluid 96. The fluid conduit 90 serves as an extension of the sensing conduit 84 above the pressure transducer 90. In the preferred embodiment, the sensing fluid 96 is a supply of sterile saline, although other fluids are contemplated. As illustrated in FIG. 5, the supply bag 94 is elevated above the mid-axillary line 58 of the patient such that the sensing fluid 96 is pressurized. Alternatively, the supply bag 94 may be pressurized with a pressure cuff, which is a standard procedure when measuring blood pressure. Yet another possibility is to use the pressure transducer 90 without the supply bag 94 and inject a volume of sterile saline into the transducer three-way connector from time to time to flush the conduits and the naso-enteral tube 14.

When the liquid feed solution is being supplied to the patient from the supply bag 20, the liquid feed solution is directed to the patient through the supply conduit 26 at a programmable rate. As the liquid feed solution is being pumped through the supply conduit 26, a volume of the sensing fluid 96 flows through the pressure transducer 90 and into the supply conduit 26 through the sensing conduit 84 to create a continuous flow of the sensing fluid. As an example, the flow of the sensing fluid 96 is typically in the range of 3 ml/hour to create continuous flushing of the pressure transducer 90. Since the sensing fluid 96 is preferably sterile saline, the low flow rate of the sensing fluid 96 into the patient has no effect on the health of the patient.

As illustrated in FIG. 5, when the pressure transducer 90 is positioned aligned with the mid-axillary line 58 of the patient, the pressure of the sensing fluid within the sensing conduit 84 is directly related to the IAP of the patient. The pressure of the sensing fluid determined by the pressure transducer 90 can then be displayed on the display screen 57 of the patient monitor 56.

When the pressure transducer 90 is positioned at the mid-axillary line 58 of the patient, the total pressure Pt sensed in the sensing conduit 84 equals the IAP for the patient plus a pressure difference of $dP = F \times R$ where F is the flow rate of the feed solution and R is the flow resistance. The pressure transducer 90 senses the pressure of the sensing fluid within the sensing conduit 84 and generates a signal based upon the sensed pressure. At low flow rates, dP will be small compared to the intra-gastric pressure and the pressure will closely reflect IAP. At high flow rates, or if the supply conduit 26 or the feeding tube 14 are obstructed, dP may give rise to a substantial overestimation of IAP. For this reason, the operation of the feeding pump 34 should be stopped from time to time in order to determine the correct IAP value and to detect any obstruction of the supply conduit 26 or the feeding tube 14.

Figure 5A:
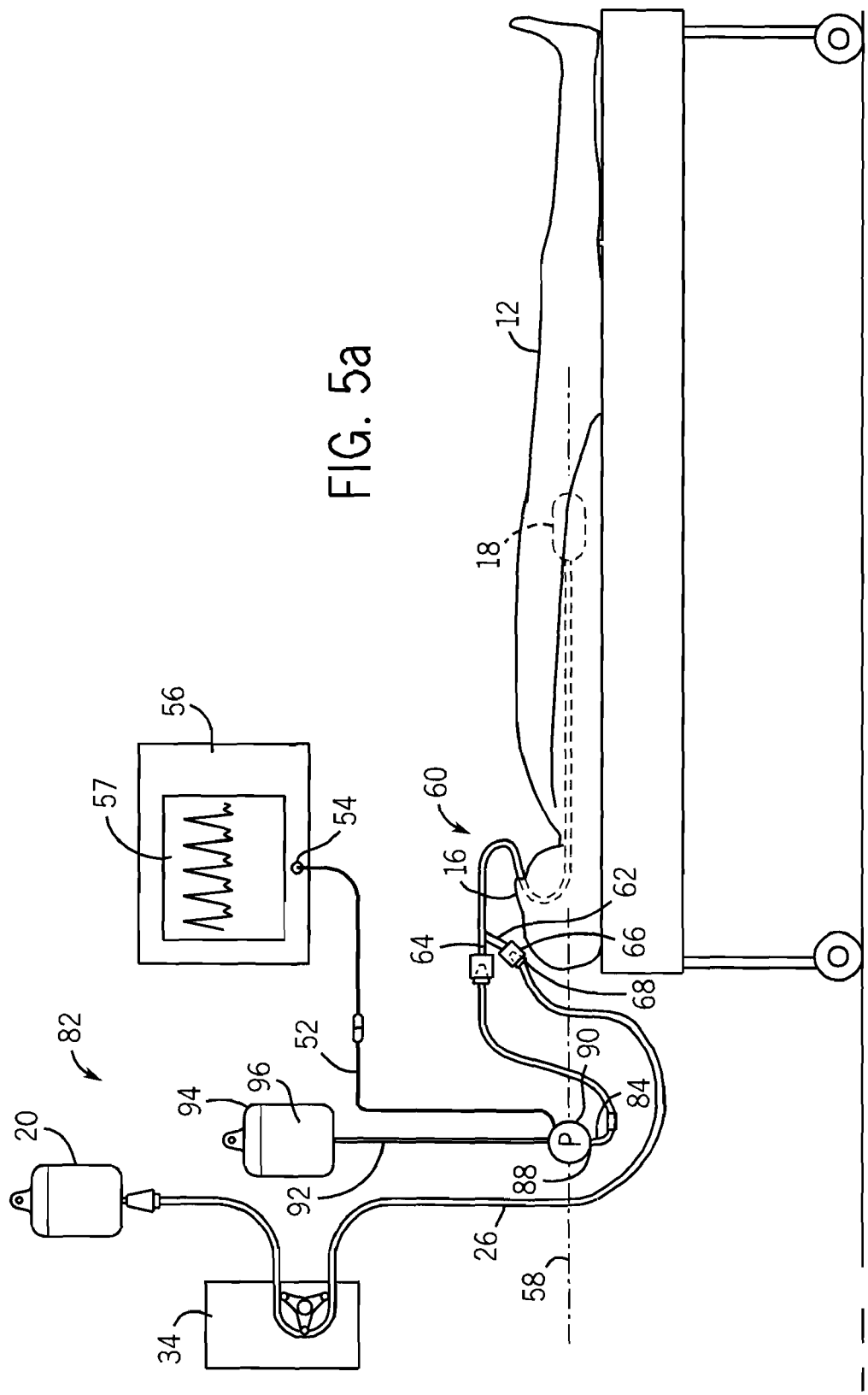
FIG. 5a is an alternate configuration of the embodiment shown in FIG. 5 in which the naso-enteric feeding tube is a dual-lumen feeding tube similar to the embodiment shown in FIG. 2.

FIG. 5a illustrates an additional embodiment in which the naso-enteral feeding tube 14 of FIG. 5 is replaced by a specialized feeding tube 60 similar to the feeding tube 60 shown in FIG. 2. As described previously, the feeding tube 60 is a dual-lumen feeding tube that includes a first lumen 62 and a second lumen 64. The first lumen 62 includes the female connector 66 that receives a mating male connector 68 of the supply conduit 26. The first lumen 62 extends into the patient's stomach or small intestines and supplies the liquid feed solution to the patient 12.

The second lumen 64 includes a first end that extends into the patient's stomach or small intestines and has a second end that extends out of the patient and receives the sensing conduit 84. As in the embodiment shown in FIG. 5, the second end 88 of the sensing conduit 84 receives the pressure transducer 90. The pressure transducer 90 receives the fluid conduit 92 extending from the supply bag 94, which includes the sensing fluid 96.

When the liquid feed solution is being supplied to the patient from the supply bag 20, a volume of the sensing fluid 96 flows through the pressure transducer 90 and into the naso-enteral tube 60 through the second conduit 64. However, in the embodiment shown in FIG. 5a, the feeding pump 34 can either be eliminated or disconnected, since the sensing fluid 96 is fed to the second lumen 64 and does not require the flow of the feeding solution through the first lumen 62. Thus, the embodiment shown in FIG. 5a can determine the IAP pressure of the patient either with or without the operation of the feeding pump 34.

In addition to sensing the IAP pressure of the patient, the system and apparatus shown in FIGS. 5 and 5a can be utilized to provide intermittent flushing of the pressure transducer 90, the sensing conduit 84, the supply conduit 26 and the naso-enteric feeding tube 14. Specifically, if flushing of the system is required, the flushing rate on the pressure transducer 90 is activated and the sensing fluid 96 is allowed to flow through the pressure transducer 90 and sensing conduit 84 at the high flushing rate. The relatively high flow rate of the sensing fluid, such as saline, flushes the components of the system. As can be understood by the above description, if the supply of sensing fluid within the pressurized supply bag 94 is sufficient, the sensing fluid 96 can fill the entire supply conduit 26 and feeding tube 14 such that the IAP of the patient can be determined by utilizing only the sensing fluid without the liquid feed solution.

Referring now to FIG. 6, thereshown is another embodiment that utilizes the elevated supply bag 94 of the sensing fluid 96 to determine the IAP for the patient 12. However, in the embodiment shown in FIG. 6, the female connector 32 of the feeding tube 14 receives a pressure adapter 98. The pressure adapter 98 includes a main body 100 having a male connector received within the female connector 32 and a female connector 102 that receives the male connector 30 formed as part of the supply conduit 26. Thus, the supply of liquid feed solution from the supply bag 20 is pumped by the feeding pump 34 through the body 100 of the pressure adapter 98 and into the feeding tube 14.

As shown in FIG. 6, the sensing conduit 84 enters into the main body 100. Preferably, the sensing conduit 84 is integrally formed with the patient adapter 98 such that the entire combination of the patient adapter 98 and the sensing conduit 84 can be supplied as a single, disposable unit.

As described with the embodiment shown in FIG. 5, the pressure transducer 90 is aligned with the mid-axillary line 58 of the patient to obtain a pressure measurement of the sensing fluid within the sensing conduit 84 as received from the supply bag 94.

Referring now to FIG. 7, thereshown is yet another embodiment of the invention. In the embodiment shown in FIG. 7, the sensing conduit 84 is a vertically positioned, transparent manometer tube 104 that is in fluid communication with the supply conduit 26. The manometer tube 104 includes an air filter 106 mounted near the second end 108 that allows for equilibrium between the interior of the manometer tube 104 and atmosphere while preventing contamination of the fluid contained within the manometer tube 104.

As shown in FIG. 7, the sensing conduit 84 is in fluid communication with the supply conduit 26 at the sensing point 40. Since the manometer tube 104 is vented to atmosphere through the air filter 106, the feeding solution will enter the sensing conduit 84. The height of the feeding solution fluid column 110 in the manometer tube reflects the IAP for the patient. The level of the fluid column 110 can be measured utilizing a measuring device 112, such as a ruler. When measuring the height of the fluid column 110, a zero marking on the ruler 112 is aligned with the mid-axillary line 58 and the height of the fluid column 110 is thus measured above the mid-axillary line 58. Alternatively, the manometer tube 104 can include a scale printed directly on the manometer tube 104 and a zero marking on the manometer tube is aligned with the mid-axillary line 58 prior to measurement of the fluid column 110.

Like the embodiments described previously, the height of the fluid column Pt in the manometer tube 104 equals the intra-gastric pressure plus a pressure difference $dP=F \times R$ where F is the flow rate of the feed solution and R is the flow resistance. As described previously, the feeding pump 34 should be stopped from time to time in order to determine both the correct IAP and to detect any obstruction in the supply conduit 26 or the feeding tube 14.

Although multiple embodiments for the present invention have been shown and described in the Figures, it is contemplated by the inventor that various other methods and apparatus can be utilized for sensing the intra-abdominal pressure of a patient utilizing the pressure of a liquid being supplied to the patient through a naso-enteric feeding tube.

I claim:

1. A method of determining the intra-abdominal pressure (IAP) in a patient having a naso-enteric tube, the method comprising the steps of:
    pumping a liquid feed solution from a supply of liquid feed solution into the patient through a supply conduit coupled to the naso-enteric tube
    positioning a sensing conduit in fluid communication with the naso-enteric tube;
    continuously flowing a sensing fluid from a supply of sensing fluid separate from the supply of liquid feed solution into the naso-enteric tube through the sensing conduit, wherein the sensing fluid flows into the gastro-intestinal tract of the patient through the naso-enteric tube;
    positioning a pressure transducer within the sensing conduit for continuously measuring the pressure of the sensing fluid within the sensing conduit; and
    continuously determining the intra-abdominal pressure of the patient based upon the measured pressure of the sensing fluid.

2. The method of claim 1 wherein the sensing fluid is a supply of saline.

3. The method of claim 1 further comprising the step of aligning the pressure transducer with a mid-axillary line of the patient.

4. The method of claim 1 wherein the supply of the sensing fluid is elevated above a mid-axillary line of the patient to pressurize the sensing fluid above the IAP of the patient.

5. The method of claim 3 wherein the supply of the sensing fluid is elevated above the mid-axillary line of the patient such that the sensing fluid is pressurized above the IAP of the patient.

6. The method of claim 1 wherein the sensing fluid continuously flows into the naso-enteric tube through the supply conduit.

7. The method of claim 1 further comprising the step of displaying the determined IAP on a patient monitor.

8. A method of determining the intra-abdominal pressure (IAP) of a patient having a naso-enteric tube to supply a liquid feed solution to the patient, the method comprising the steps of:
    pumping the liquid feed solution from a supply of liquid feed solution into the patient through the naso-enteric tube;
    positioning a sensing conduit in fluid communication with the liquid feed solution pumped into the patient;
    continuously flowing a sensing fluid from a supply of sensing fluid separate from the supply of liquid feed solution into the naso-enteric tube through the sensing conduit;
    continuously measuring the pressure of the sensing fluid; and
    continuously determining the IAP of the patient based upon the measured pressure of the sensing fluid.

9. The method of claim 8 wherein the sensing conduit extends between a first end and a second end, the first end being in communication with the flow of liquid feed solution and the second end being coupled to a pressure transducer operable to detect the pressure of the sensing fluid.

10. The method of claim 9 further comprising the step of positioning the pressure transducer in alignment with a mid-axillary line of the patient.

11. A system for determining the intra-abdominal pressure (IAP) of a patient having a naso-enteric tube, the system comprising:
    a supply conduit positioned between the naso-enteric tube and a supply of liquid feed solution to provide the liquid feed solution to the gastro-intestinal tract of the patient through the naso-enteric tube;
    a sensing conduit in fluid communication with the naso-enteric tube;
    a supply of a sensing fluid separate from the supply of liquid feed solution and pressurized above the IAP of the patient and positioned to provide a continuous flow of the sensing fluid into the naso-enteric tube through the sensing conduit such that the continuous flow of sensing fluid flows into the gastro-intestinal tract of the patient through the naso-enteric tube; and
    a pressure transducer positioned to receive the continuous flow of the sensing fluid, wherein the pressure transducer continuously determines the pressure of the sensing fluid within the sensing conduit.

12. The system of claim 11 further comprising:
    a pressure adapter having a first end configured to receive the supply conduit and a second end configured to be received by the naso-enteric tube,
    wherein the pressure adapter receives the sensing conduit between the first and second ends of the pressure adapter such that the sensing fluid flows through the pressure adapter and into the naso-enteric tube.

13. The system of claim 11 wherein the sensing conduit includes means for receiving the supply conduit.

14. The method of claim 8 further comprising the steps of:
    elevating the supply of the sensing fluid above the mid-axillary line of the patient such that the sensing fluid is pressurized above the IAP of the patient; and
    continuously flowing the sensing fluid into the naso-enteric tube through the pressure transducer.

15. The method of claim 1 wherein the pressure transducer is positioned such that the sensing fluid flows through the pressure transducer and into the naso-enteric tube.

16. The system of claim 11 wherein the pressure transducer is positioned such that the continuous flow of the sensing fluid flows through the pressure transducer.

17. A method of determining the intra-abdominal pressure (IAP) in a patient having a naso-enteric tube, the method comprising the steps of:
provide a pressure adapter having a first end and a second end, wherein the second end receives the naso-enteric tube;
positioning a sensing conduit in fluid communication with the pressure adapter between the first and second end of the pressure adapter;
continuously flowing a sensing fluid from a supply of sensing fluid into the naso-enteric tube through the sensing conduit and the pressure adapter, wherein the sensing fluid flows into the gastro-intestinal tract of the patient through the pressure adapter and the naso-enteric tube;
selectively coupling a supply conduit to the first end of the pressure adapter, wherein the supply conduit is positioned to supply a liquid feed solution from a supply of liquid feed solution separate from the supply of sensing fluid to the gastro-intestinal tract of the patient through the pressure adapter and the naso-enteric tube;
positioning a pressure transducer within the sensing conduit for continuously measuring the pressure of the sensing fluid within the sensing conduit; and
continuously determining the intra-abdominal pressure of the patient based upon the measured pressure of the sensing fluid.

* * * * *